(12) United States Patent
Li et al.

(10) Patent No.: US 8,257,918 B2
(45) Date of Patent: Sep. 4, 2012

(54) INTELLIGENT NANOMEDICINE INTEGRATING DIAGNOSIS AND THERAPY

(75) Inventors: Na Li, Los Angeles, CA (US); Winny Tan, Fremont, CA (US)

(73) Assignee: The Regents of the University of California, Oakland, CA (US)

( * ) Notice: Subject to any disclaimer, the term of this patent is extended or adjusted under 35 U.S.C. 154(b) by 959 days.

(21) Appl. No.: 11/631,738

(22) PCT Filed: Jul. 7, 2005

(86) PCT No.: PCT/US2005/024377
§ 371 (c)(1),
(2), (4) Date: Dec. 3, 2007

(87) PCT Pub. No.: WO2006/019637
PCT Pub. Date: Feb. 23, 2006

(65) Prior Publication Data
US 2009/0202507 A1    Aug. 13, 2009

Related U.S. Application Data

(60) Provisional application No. 60/586,373, filed on Jul. 7, 2004.

(51) Int. Cl.
*C12Q 1/68* (2006.01)
*C07H 21/04* (2006.01)
*C07H 21/02* (2006.01)

(52) U.S. Cl. ..... 435/6; 536/23.1; 536/24.31; 536/24.33; 536/24.5

(58) Field of Classification Search ........................ None
See application file for complete search history.

(56) References Cited

OTHER PUBLICATIONS

Park et al. (Journal of Clinical Microbiology, Aug. 2000, vol. 38, No. 8, pp. 2829-2836).*
Stojanovic et al. (Chembiochem 2001, 2, 411-415).*

* cited by examiner

*Primary Examiner* — Amy Bowman
(74) *Attorney, Agent, or Firm* — Berliner & Associates

(57) ABSTRACT

A method of controlling the activity of a biologically active compound. The method concerns an oligonucleotide-based compound, comprising a hairpin-forming oligonucleotide, an effector moiety physically associated with the oligonucleotide, where the effector moiety possesses a biological activity, and a regulating moiety physically associated with the oligonucleotide, where the regulating moiety controls the biological activity of the effector moiety by interacting with the effector moiety. The oligonucleotide can assume a hairpin configuration, where the effector and regulating moieties interact, or an open configuration, where the effector and regulating moieties fail to interact. Depending on the nature of the effector and regulating moieties, either configuration can result in the expression of the biological activity of the effector moiety.

19 Claims, 6 Drawing Sheets

A: "Diagnosis" loop  B: Blocking structure

C: Porous drug capsule  D: Biomarker

E: Released drug (a) HMR 1826

(b) Leu-Dox

INTELLIGENT NANOMEDICINE INTEGRATING DIAGNOSIS AND THERAPY

CROSS-REFERENCE TO RELATED APPLICATIONS

This application claims the benefit of U.S. Provisional Application No. 60/586,373, filed on Jul. 7, 2004.

STATEMENT REGARDING FEDERALLY SPONSORED RESEARCH OR DEVELOPMENT

This invention was made with Government Support under Grant No. NCC2-1364, awarded by the NASA Ames Research Center, and Grant No. NIDCR DE 15018, awarded by the National Institute of Health. The Government has certain rights in this invention.

REFERENCE TO A SEQUENCE LISTING

This application includes a Sequence Listing submitted electronically via EFS-Web as a text file named "1279424SeqList.txt", with a creation date of Jul. 23, 2012 and a file size of 17.175 kilobytes. The sequence listing is incorporated by reference herein in its entirety.

BACKGROUND

1. Field of Invention

This invention relates generally to hairpin-forming oligonucleotides.

2. Related Art

With the rapid advances of modem pharmacology, effective drugs have been discovered for many diseases. However, many of these drugs have undesirable side effects due to their poor distinction between sick cells and healthy cells. For instance, many chemotherapy agents act on cancer cells that are actively dividing and replicating. Unfortunately, these agents do not discriminate between cancer cells and actively dividing normal cells such as blood cells forming bone marrow, cells in the digestive tract, hair follicles, and reproductive cells. As such, the effectiveness of these drugs is limited because dosage levels and treatment frequency cannot exceed the tolerance levels of normal cells.

One approach to minimizing the side effects of a drug is to target processes predominantly associated with disease states. For example, angiogenesis is essential for tumor growth but less essential in the normal adult. Therefore, compounds that target angiogenesis may be less toxic. Similarly, compounds that limit tumor metastasis may have less side effects. Notwithstanding these and other approaches to drug development, there is a continuing need to develop drugs having reduced side effects.

SUMMARY

The present invention concerns an "intelligent" oligonucleotide-based compound that can be activated in sick cells, but not healthy cells, due to the integration of diagnostic and therapeutic functions into the compound. The diagnostic function discriminates between healthy and sick cells and is continuously performed by recognizing a biomarker for a specific disease. A biomarker is a molecule such as a protein, an RNA or DNA, or small organic molecule that is associated with a disease state. When the amount of biomarker changes, the oligonucleotide-based compound can change its conformation, either activating or deactivating the therapeutic functions incorporated into the compound. Thus, the oligonucleotide-based compound can intelligently adjust its dosage according to the amount of biomarker present in a cell.

In one aspect, the present invention provides a method of controlling the activity of a biologically active compound. The method comprises: a) providing a hairpin-forming oligonucleotide capable of existing in either a hairpin configuration having a single-stranded loop and a double-stranded stem, or an open configuration lacking the double-stranded stem; b) physically associating an effector moiety with the oligonucleotide, where the effector moiety possesses a biological activity; c) physically associating a regulating moiety with the oligonucleotide, where the regulating moiety controls the biological activity of the effector moiety when the regulating and effector moieties interact; and d) changing from one configuration to the other. The regulating moiety can interact with the effector moiety when the oligonucleotide is in the hairpin configuration, while the regulating and effector moieties fail to interact when the oligonucleotide is in the open configuration.

In another aspect, the present invention provides an oligonucleotide-based compound, comprising: a) a hairpin-forming oligonucleotide; b) an effector moiety physically associated with the oligonucleotide, where the effector moiety possesses a biological activity; and c) a regulating moiety physically associated with the oligonucleotide, where the regulating moiety controls the biological activity of the effector moiety by interacting with the effector moiety. The regulating moiety can interact with the effector moiety when the oligonucleotide forms a hairpin structure having a single-stranded loop and a double-stranded stem. The regulating and effector moieties fail to interact when the oligonucleotide takes an open configuration lacking the double-stranded stem.

The oligonucleotide-based compound of the present invention provides a way to regulate the biological and therapeutic activities of a biologically active compound. Depending on the nature of the effector and regulating moieties, the biological activity of the effector moiety can be expressed in either the hairpin or open configurations.

Other embodiments of the invention include a pharmaceutical composition containing an oligonucleotide-based compound of the present invention, and a method of treating cancer by administering an oligonucleotide-based compound to a patient.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Figure 1:
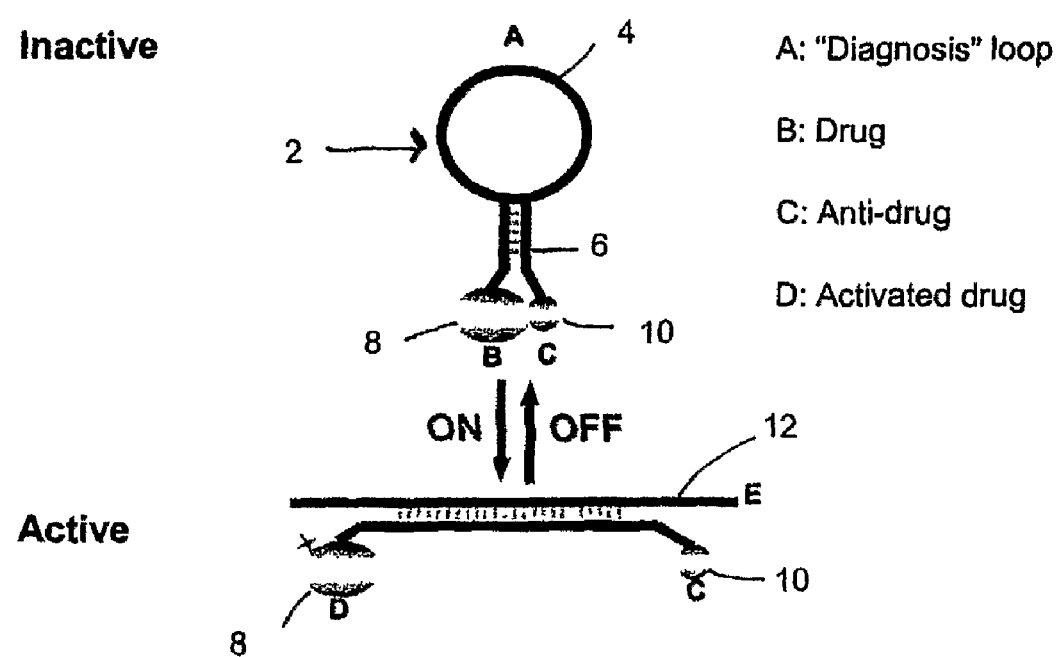
FIG. 1 is a schematic drawing of an oligonucleotide-based compound that is active in the open configuration.

In accordance with the present invention, an effector moiety and a regulating moiety are associated with a hairpin-forming oligonucleotide. As is well known, the hairpin configuration of an oligonucleotide comprises a single-stranded loop region and double-stranded, or duplex, stem region. Under certain conditions, the duplex stem does not form and the oligonucleotide then assumes an open, or non-hairpin, configuration. For example, under low salt or high temperature conditions, the stability of the duplex stem can be reduced sufficiently such that the oligonucleotide assumes an open configuration. In certain embodiments of the present invention, the binding of a biomarker to the loop region of the oligonucleotide produces a biomarker-loop combination that overcomes the duplex stem, resulting in an open configuration.

In other embodiments, the oligonucleotide forms an open structure when the single-stranded loop region binds to a molecule provided as a binding partner for the oligonucleotide. In certain embodiments, the binding partner is designed to bind to either the single-stranded loop of the oligonucleotide or a biomarker, and is designed to bind more strongly to the biomarker than to the single-stranded loop. In this way, when the biomarker is present, the binding partner forms a biomarker-binding partner hybrid. This removes the binding partner from the oligonucleotide, which can now assume a hairpin configuration. The change in structure allows the regulating moiety to interact with the effector moiety. The binding-partner is provided as a further component of the oligonucleotide-based compound of the present invention.

An effector moiety is a small molecule, large molecule, or molecular complex that can carry out or influence a biological process, or, upon interaction with a regulating moiety, can be converted to a substance that can carry out or influence a biological process. Examples of effector moieties include, but are not limited to: enzymes, which catalyze biological reactions; proteins that bind ligands; drugs and prodrugs, which alter physiological and cellular processes; anti-sense molecules, which prevent gene expression in cells; and molecular complexes that release stored drugs or prodrugs. A biological process is a process that can occur in cells or in organisms.

The term "biological activity" means the ability of an effector moiety to carry out or influence, or be converted to carry out or influence, a biological process. Biological activity therefore depends on the nature of the particular effector moiety and the biological process carried out or influenced by the particular effector moiety. Preferably, the biological activity is a "therapeutic activity", which means a biological activity directed to the treatment of a disease or condition in a patient. For example, when the disease is cancer, the therapeutic activity can be a biological activity directed to preventing the proliferation of cancer cells, or directed to inhibiting angiogenesis. When the disease state is a vascular condition such as myocarditis, which involves the inflammation of the myocardium and loss of contractile myocytes dues to apoptosis and necrosis, the therapeutic activity can be a biological activity directed to preventing apoptosis.

The regulating moiety controls the biological activity of the effector moiety. The way the regulating moiety exerts this control is varied and depends on the nature of the effector moiety. For example, when the effector moiety comprises an enzyme, the regulating moiety can control the activity of the enzyme by inhibiting or activating the protein. When the effector moiety comprises a prodrug, the regulating moiety can control the conversion of the prodrug into a therapeutically active agent. When the effector moiety comprises a drug, or contains a drug, the regulating moiety can control the release of the drug. An antisense molecule can be controlled by hybridizing the antisense sequence to a regulating moiety having a sequence complementary to the antisense sequence. Other examples will be apparent to those skilled in the art.

A biomarker is a molecule or substance associated with a disease state of a cell or tissue. Examples of biomarkers include, but are not limited to, a mutated protein or RNA, an amplified gene, an abnormally modified protein or RNA, an over-expressed protein or RNA, and high levels of ATP or $Ca^{2+}$. Specific examples of biomarkers useful in cancer therapy include mutated ras protein and RNA in cancer cells of the colon or lung, over-expressed epidermal growth factor receptor protein and RNA in prostate, breast and colorectal cancer cells, and over-expressed vascular endothelial growth factor protein and RNA in breast or pancreatic cancer cells. In normal cells, the biomarker is absent or present in limited amounts. In such cells, the oligonucleotide-based compound is inactive—that is, the biological activity of the effector moiety is not expressed. When the biomarker is present in unhealthy cells, the oligonucleotide-based compound is turned on, and the effector moiety expresses its biological activity.

One embodiment of the present invention is shown in FIG. 1. In this embodiment, the oligonucleotide-based compound 2 forms a hairpin-structure having a single-stranded loop 4 and double-stranded stem region 6, similar to a molecular beacon, with an effector moiety 8 comprising an enzyme and a regulating moiety 10 comprising an inhibitor of the enzyme. The inhibitor can occupy or block the active site of the enzyme, or bind to an allosteric site on the enzyme. The loop region 4 of the oligodeoxynucleotide-based compound has a sequence complementary to a portion of the nucleotide sequence of a biomarker 12, which in this case is a mutant mRNA or an over-expressed gene. When not hybridized to the biomarker, the oligonucleotide-based compound is in the hairpin-configuration and the drug cannot work with its inhibitor in close proximity—the oligonucleotide-based compound is inactive. When the loop region binds to the biomarker, the oligonucleotide-based compound opens up and separates the enzyme and inhibitor, thereby freeing the enzyme to act—the oligonucleotide-based compound is now active.

Figure 2:
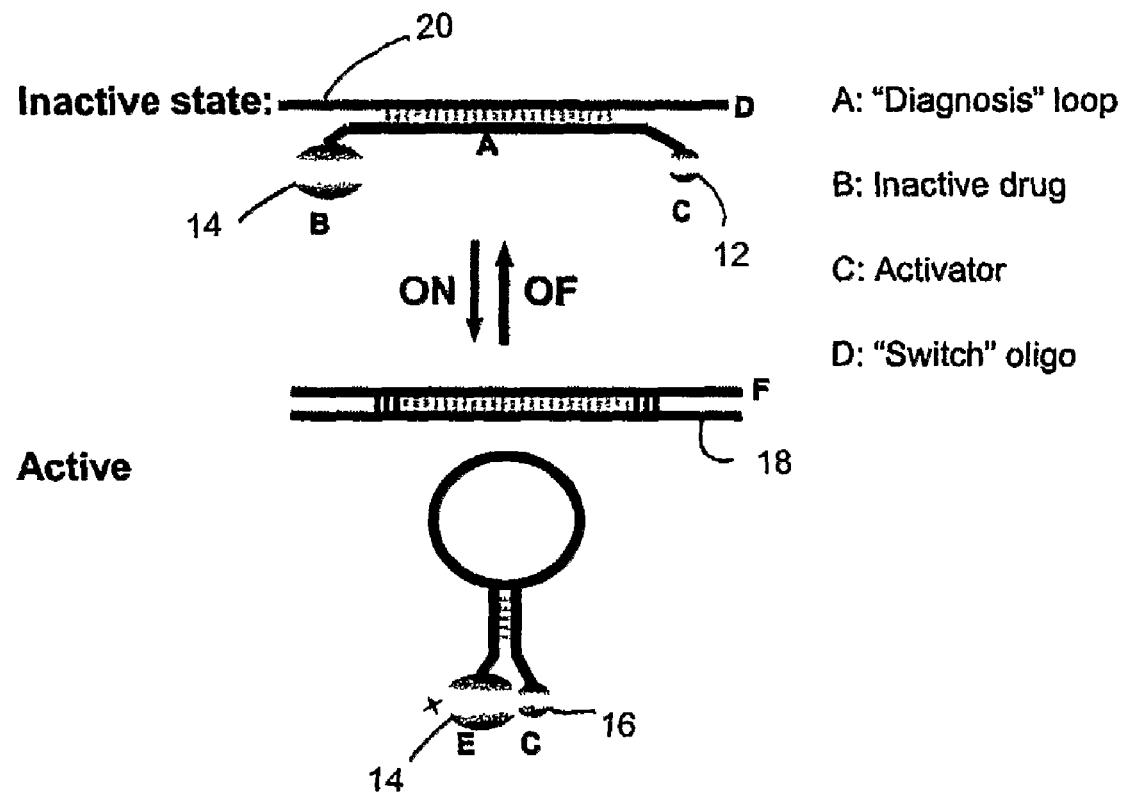
FIG. 2 is a schematic drawing of an oligonucleotide-based compound that is active in the hairpin configuration.

Another embodiment of the present invention is shown in FIG. 2. In this embodiment, the effector moiety 14 is a prodrug and the regulating moiety 16 is an enzyme that converts the prodrug into an active agent. The open and hairpin configurations of the oligonucleotide-based compound correspond to the inactive and active states. That is, in the open configuration, the enzyme and prodrug are too far apart for the enzyme to convert the prodrug into an active agent; thus, the oligonucleotide-based compound is inactive. When a hairpin structure is formed, the enzyme acts on the prodrug, converting it into an active agent; thus, the oligonucleotide-based compound is active. The biomarker 18 is a mutant mRNA or an over-expressed gene.

This embodiment includes a binding partner 20 for the oligonucleotide. The binding partner binds to the loop of the oligonucleotide-based compound, thus keeping the compound in the open, inactive configuration. The binding partner is complementary to both the loop sequence and to the biomarker sequence. Further, the binding partner is designed to have higher affinity for the biomarker than for the loop sequence. Thus, in the presence of the biomarker, the binding partner binds to the biomarker instead of the loop. This allows the oligonucleotide-based compound to assume the hairpin, active configuration. Therefore, in the presence of the biomarker, the oligonucleotide-based compound is active.

The binding partner is designed to bind to both the loop region of the oligonucleotide and the biomarker. When a binding partner is provided and the biomarker is RNA or DNA, the loop and the biomarker will generally have similar nucleotide sequences. The binding partner is designed to bind more strongly to the biomarker than the loop. One way that this differential binding can be accomplished is to have the binding partner form a longer region of hybridization with the biomarker than with the loop. The design of oligonucleotide sequences for the binding partner, biomarker and loop can be performed by nucleotide sequence programs well known in the art.

In those embodiments where the loop region of a hairpin-forming oligonucleotide recognizes a biomarker, it will be appreciated that the form of the loop region can depend on the nature of the biomarker. For example, the loop region can be a triple helix-forming oligonucleotide to target DNA, an antisense oligonucleotide to target mRNA, or an aptamer to target protein or small molecules such as ATP. Examples and design of triple helix-forming oligonucleotides are found in U.S. Pat. No. 6,403,302 to Dervan et al., herein incorporated by reference. Examples and design of antisense oligonucleotides are found in U.S. Pat. No. 6,869,795 to Bartelmez et al., herein incorporated by reference. Examples and design of aptamer sequences are found in U.S. Pat. No. 6,867,289 to Gorenstein et al., herein incorporated by reference.

The oligonucleotide-based compounds of the present invention have structures similar to those of molecular beacons. Molecular beacons are based on hairpin-forming oligonucleotides, as described in U.S. Pat. No. 6,037,130 to Tyagi et al, incorporated by reference herein. However, in contrast to molecular beacons, which contain a pair of fluorophores and a quencher, the present invention provides oligonucleotide-based compounds containing effector moieties having biological activities and regulating moieties controlling those biological activities.

The design of hairpin-forming oligonucleotides is discussed by Tyagi et al. in U.S. Pat. No. 6,037,130. The oligonucleotide sequences of the hairpin-forming oligonucleotides of the present invention can be DNA, RNA, peptide nucleic acid (PNA) or combinations thereof. Preferably, the oligonucleotides are DNA or RNA, and more preferably, RNA. Modified nucleotides may be included, for example nitropyrole-based nucleotides or 2'-O-methylribonucleotides. Modified linkages also may be included, for example phosphorothioates. The hairpin-forming oligonucleotides of the present invention can be prepared by any method well known in the art. Preferably, the oligonucleotides are prepared by automated synthesis.

As used herein, the term "oligonucleotide" includes derivatives thereof, such as backbone modifications, e.g., phosphorothioate derivatives, employed to stabilize the oligonucleotide. All such modifications are contemplated equivalents of the hairpin-forming oligonucleotides of the invention. The following discussion provides examples of the kinds of modifications that may be employed, but those of skill in the art will readily recognize others. Non-naturally occurring backbones may be substituted for DNA oligonucleotides; such backbones can be more stable than native DNA. For example, the oligonucleotides may be provided in stabilized form, e.g. with phosphotriester linkages, or by blocking against exonuclease attack with methylphosphonodiester linkages, with 3' deoxythymidine, as a phenylisourea derivative, or by linking other molecules such as aminoacridine or polylysine to the 3' end of the oligonucleotide. Base analogues can be substituted for the commonly found A (adenosine or deoxyadenosine), G (guanosine or deoxyguanosine), C (cytidine or deoxycytidine), or T (thymine). Examples include, but are not limited to, 7-aza-G and 5-methyl-C. Such base analogues are useful for adjusting the melting temperature of an oligonucleotide, or a segment thereof. Substitution of rT (ribothymidine) for U or dU (deoxyuridine) for T are also possible.

In accordance with the present invention, the length of the loop sequence, the length of the duplex stem, and the relation of the two are designed according to the biomarker, any binding partner, and the particular regulating and effector moieties to be utilized. Lengths of biomarker-recognizing sequence and stem hybrid for particular conditions can be estimated by known means, and experimentally tried and adjusted, if necessary. Generally, the loop sequences for use in the oligonucleotide-based compounds are in the range of 16 to 30 nucleotides. Typical stem lengths are in the range of 3 to 8, more commonly 4 to 7 nucleotides. The strength of the duplex stem can be adjusted by routine experimentation to achieve proper functioning. In addition to length, the strength of the duplex stem can be adjusted by altering the G-C content and insertion of destabilizing mismatches, as will be appreciated. One strand of the duplex stem is considered to be complementary to the other strand as long as the strands hybridize. A complementary strand can be completely complementary, or have mismatches that nonetheless allow a duplex to form. A strand having a sequence that is completely complementary to the other strand is said to be "perfectly" complementary.

A binding partner is a molecule that binds to the loop of the hairpin-forming oligonucleotide, resulting in an open structure. The binding partner can be a protein, oligonucleotide, or other small molecule, so long as the binding partner causes the hairpin-forming oligonucleotide to form an open structure. Preferably, the binding partner is an oligonucleotide. Similar to the hairpin-forming oligonucleotides, the binding partner can be DNA, RNA, peptide nucleic acid (PNA) or combinations thereof. In preferred embodiments, the binding partner is DNA or RNA, and more preferably, RNA.

In designing the hairpin-forming oligonucleotides of the present invention, consideration is preferably given to the following properties: high resistance to nuclease activity; correct intracellular and subcellular delivery; low non-sequence-dependent toxicity; high specificity for biomarker; appropriate affinity for the biomarker, and good antisense effects (for effector moieties containing antisense molecules). Resistance to nuclease activity and intracellular/subcellular delivery can be attained by appropriate chemical modification of the oligonucleotides, as is well known in the art. For example, chemical modifications for nuclease resistance are described in U.S. Pat. No. 6,867,289 to Gorenstein et al., U.S. Pat. No. 6,869,795 to Bartelmez et al., and U.S. Pat. No. 6,027,892 to Chang et al., all incorporated by reference herein. Facilitated delivery can also be attained by use of liposomes or other delivery vehicles, as described in U.S. Pat. No. 6,803,360 to Chang et al., incorporated by reference herein.

High specificity and appropriate affinity for the biomarker will depend mainly on the sequence of the loop. As is well known, the design of the loop sequence and the stem sequence, as well as the design of a binding partner sequence, can be performed with the use of software for molecular beacon design or other thermodynamic prediction tools.

An effector moiety or regulating moiety can be connected to the hairpin-forming oligonucleotide or included as part of the oligonucleotide. For example, an enzyme or prodrug can be attached to the oligonucleotide by well known chemistries such as amine chemistry, thiol chemistry and hydrazine chemistry. Alternatively, an anti-sense molecule can be included as a portion of one strand of the duplex stem. In either case, the moiety is considered to be "physically associated" with the hairpin-forming oligonucleotide.

In general, depending on the chemical properties of a particular effector or regulatory moiety, the attachment of the moiety to the hairpin-forming oligonucleotide can be performed during or after synthesis of the oligonucleotide. For example, in the first case, during the synthesis of the oligonucleotide, the moiety can be directly incorporated onto the 3' of the oligonucleotide by means of a modified solid support (CPG) and onto the 5' of the oligonucleotide by means of a phosphoramidite reagent. In the second case, during the synthesis of the oligonucleotide, some functional group or groups will be added to the oligonucletide. The effector or regulating moiety can then be attached to the oligonucleotide via the incorporated functional groups. Well-known chemistries that can be used here include amine chemistry, thiol chemistry and hydrazine chemistry.

In certain cases, cross-linking reagents can be used to form molecular bridges (or linkers) that tie together functional groups of two different molecules, e.g., a protein and an oligonucleotide. To link two different molecules in a stepwise manner, hetero-bifunctional cross-linkers can be used that eliminate unwanted homopolymer formation. Suitable linkers are products of cross-linking reagents that are commercially available (e.g., Pierce Chemical Co.). A wide variety of cross-linking reagents are available that are capable of reacting with various functional groups present on the oligonucleotide and effector or regulating moiety. Thus, many chemically distinct linkages can be conjugated. Preferably, the linker is a product of a cross-linking reagent that comprises an active ester, isothiocyano, isocyano, acyl, halo, maleimido, or active disulfido group. Examples of groups that can be used for cross-linking include primary or secondary amine groups, hydrazide or hydrazine groups, carboxyl alcohol, phosphate, and alkylating groups.

The use of peptide linkers, such as L-Leu-L-Ala-L-Leu-L-Ala, is also contemplated.

As an example of the use of a cross-linking reagent, a protein or prodrug can contain a free amino group at one end of the molecule. It will react regiospecifically and site specifically with the heterobifunctional cross-linking reagent SMCC to form an amide bond. The oligonucleotide, if chemically modified to contain a free sulfhydryl group, will chemically combine with SMCC to form a thioether linkage. In this example, the linkage formed between the oligonucleotide and the effector moiety could be summarized as amide/thioether. Other linkages between the oligonucleotide and the moiety include, but are not restricted to, amide/amide, thioether/amide, disulfide/amide, amide/thioether, and amide/disulfide.

In addition to SMCC, other examples of hetero-bifunctional cross-linkers include, but are not limited to, SMPT, SPDP, LC-CPDP, Sulfo-LC-SPDP, Sulfo-SMCC, MBS, Sulfo-MBS, SIAB, Sulfo-SIAB, and EDC-Sulfo-NHS.

The effector and regulating moieties can be connected at any location along the hairpin-forming oligonucleotide provided that the attached moieties do not interfere with the hairpin-open configurations, and provided that the regulating and effector moieties can interact when the oligonucleotide is in the hairpin configuration, and fail to interact in the open configuration. Preferably, the effector moiety is attached to one end of the oligonucleotide and the regulating moiety to the other end.

Figure 3:
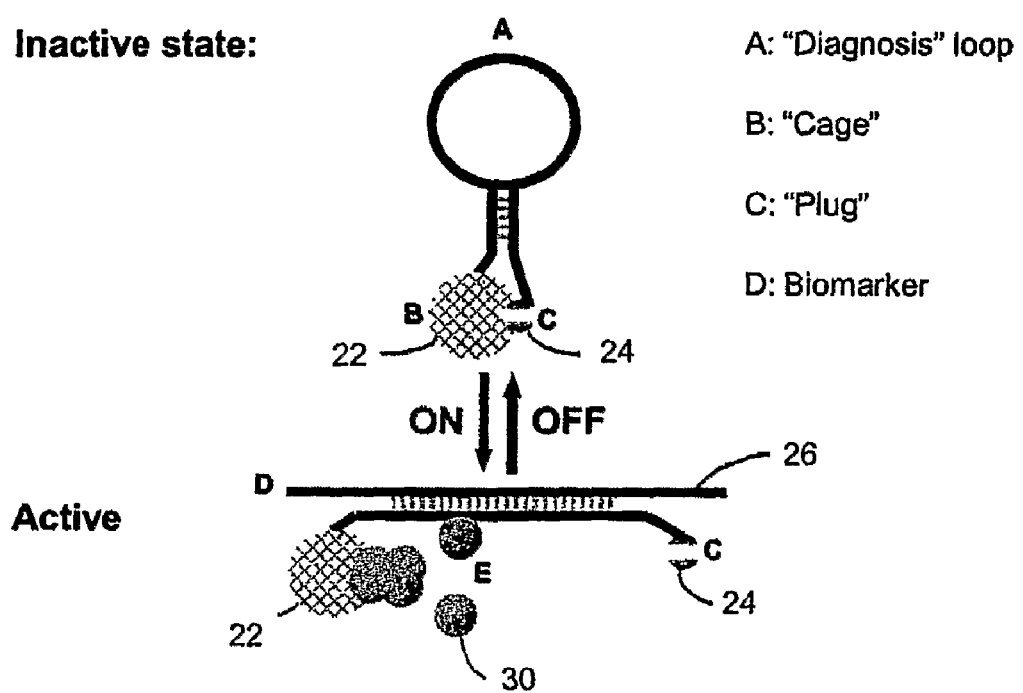
FIG. 3 is a schematic drawing of an oligonucleotide-based compound having cage and plug moieties.

Another embodiment of the present invention is shown in FIG. 3. The effector moiety in this case comprises a nanofabricated container 22 or "cage". The cage is a compartment with a small opening, filled with a drug. The regulating moiety or "plug" 24 is a structure that can block the opening, thus preventing the drug from escaping when the cage and the plug are brought together. When a biomarker 26 binds to the loop of the oligonucleotide-based compound, the compound assumes an open configuration, separating the plug from the cage. This results in drug 30 being released from the cage.

Figure 4:
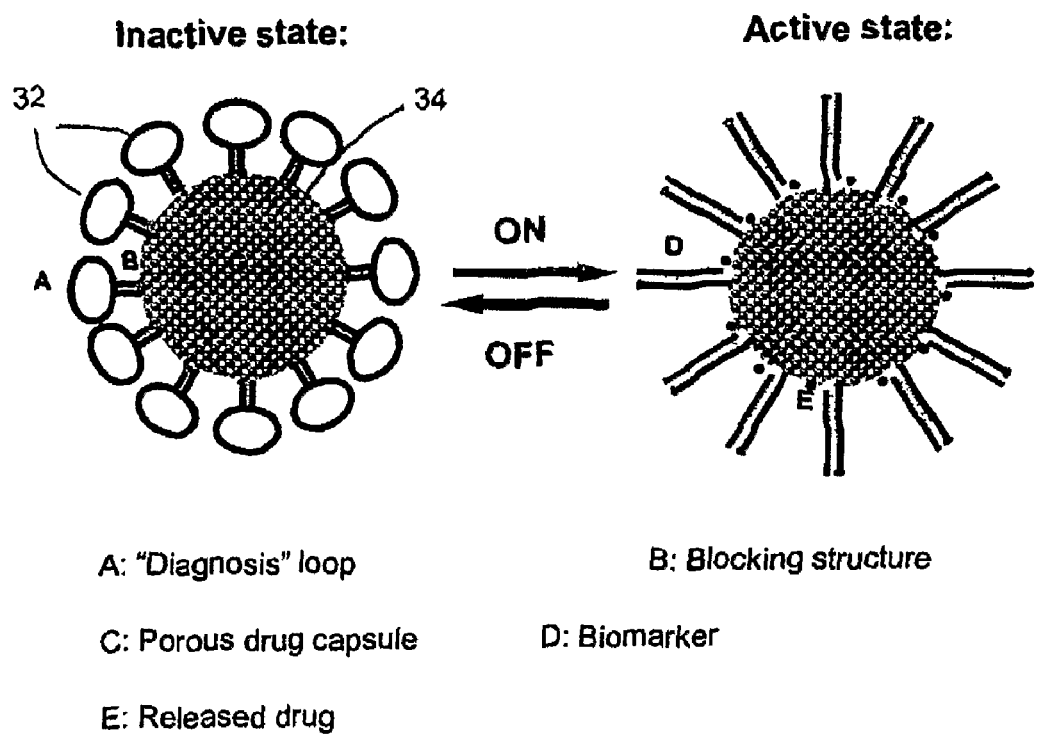
FIG. 4 is a schematic drawing of a plurality of oligonucleotide-based compounds associated with a porous drug capsule.

In further embodiment is shown in FIG. 4. This embodiment has a plurality of hairpin-forming oligonucleotides 32, each with one end immobilized on a porous drug capsule 34, which can be constructed using inorganic polymers or natural polymers such as DNA. The other end of each oligonucleotide has a blocking structure which functions similarly to the 'plug' in FIG. 3. When a biomarker binds to the loop of one or more of the oligonucleotides, the oligonucleotide assumes an open configuration, allowing the drug to be released.

Figure 5:
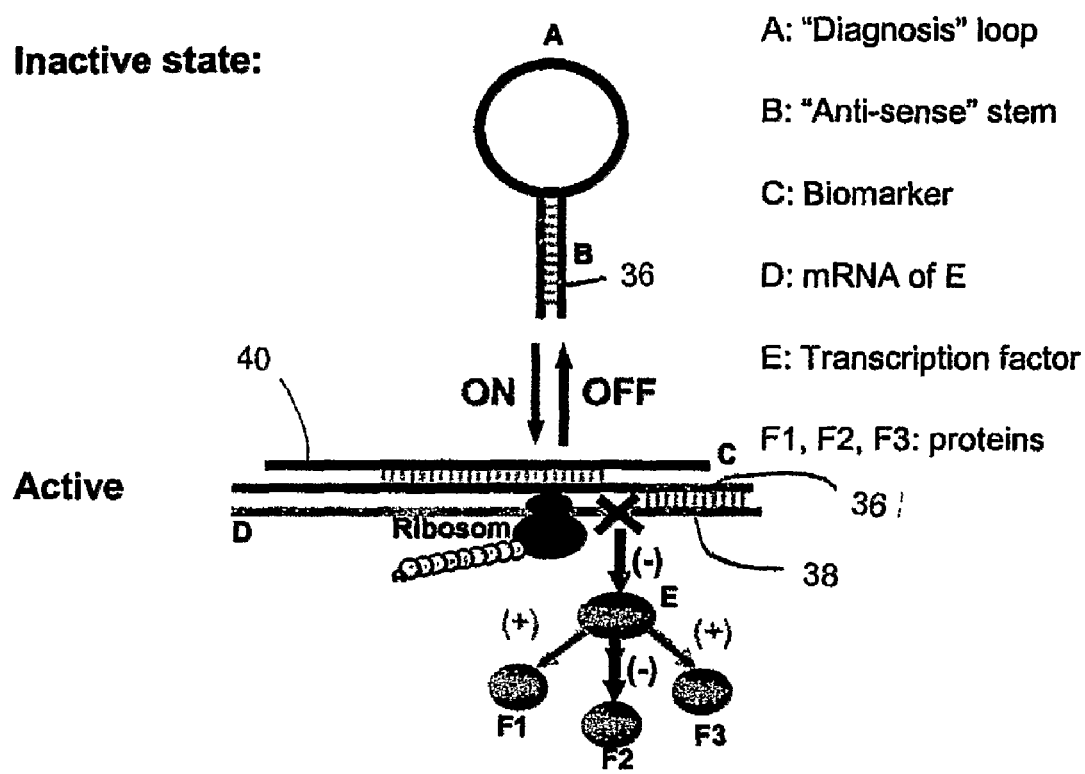
FIG. 5 is a schematic drawing of an oligonucleotide-based compound having an antisense sequence in the stem.

In another embodiment shown in FIG. 5, the effector moiety is an antisense sequence 36 incorporated into a portion of the duplex stem of a hairpin-forming oligonucleotide. The regulating moiety is a sequence complementary to the antisense sequence. If necessary, the duplex stem can be designed to have mismatches between the antisense sequence and the regulating complementary sequence such that the antisense sequence has greater affinity for the target RNA 38 than for the regulating complementary sequence. When the biomarker 40 is present, the oligonucleotide assumes an open configuration, allowing the antisense sequence to act on the target RNA.

In accordance with the present invention, an oligonucleotide-based compound of the present invention can be delivered to a diseased cell or tissue using various methods for delivering nucleic acid molecules. Techniques for in vivo delivery of foreign therapeutic nucleic acid molecules are known to those skilled in the art. Incorporated herein by reference are Zhu, et al., Science 261:209-211(1993), which describes the intravenous delivery of cytomegalovirus (CMV)-chloramphenicol acetyltransferase (CAT) expression plasmid using DOTMA-DOPE complexes; Hyde, et al., Nature 362:250-256 (1993), which describes the delivery of the cystic fibrosis transmembrane conductance regulator (CFTR) gene to epithelia of the airway and to alveoli in the lung of mice, using liposomes; and Brigham, et al., Am. J. Med. Sci. 298:278-281 (1989), which describes the in vivo transfection of lungs of mice with a functioning prokaryotic gene encoding the intracellular enzyme chloramphenicol acetyltransferase (CAT).

In preferred embodiments, the oligonucleotide-based compound is delivered as a liposome-nucleic acid complex. Techniques for the formation of cationic lipid-polynucleotide complexes are found in Nabel, et al., "Methods for Liposome-Mediated Gene Transfer to Tumor Cells in Vivo," Chapter 21, Methods in Molecular Medicine, (Ed. P. Robbins, 1997. Humana Press Inc., Totowa, N.J.; and Son, et al., "Cationic Liposome: Mediated Gene Transfer to Tumor Cells in Vitro and In Vivo," Chapter 23, Methods in Molecular Medicine, supra, both incorporated by reference herein. Additional non-limiting examples of preparing liposomes are described in U.S. Pat. Nos. 4,728,578, 4,728,575, 4,737,323, 4,533,254, 4,162,282, 4,310,505, and 4,921,706, each incorporated herein by reference.

The present invention provides a pharmaceutical composition comprising a therapeutically effective amount of an oligonucleotide-based compound of the present invention, or a pharmaceutically acceptable salt thereof. A therapeutically effective amount is an amount that results in an improvement or a desired change in condition for which the oligonucleotide-based compound is administered, when the compound is administered once or over a period of time. For example, with respect to cancer, the improvement can be reduction in the size of a tumor, or a reduction in the symptoms or discomfort associated with the cancer. As is known, the amount will vary depending on such particulars as the condition being treated, the specific oligonucleotide-based compound utilized, the severity of the condition, and the characteristics of the patient.

Pharmaceutically acceptable salts are well known in the art and include salts prepared from pharmaceutically acceptable non-toxic acids, including inorganic acids and organic acids. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, hydrochloric, hydrobromic, phosphoric, sulfuric acids, and the like. Salts formed with, for example, a free carboxy group of an amino acid residue or a peptide, can be derived from inorganic bases including, but not limited to, sodium, potassium, ammonium, calcium or ferric hydroxides, and organic bases including, but not limited to, isopropylamine, trimethylamine, histidine, and procaine.

A pharmaceutical composition of the present invention will typically contain a pharmaceutically acceptable carrier. Various means of administration are contemplated, such as oral, nasal, topical, rectal, inhalation, intramuscular, intravenous, intraperitoneal, and the like. Depending on the intended mode of administration, the pharmaceutical compositions may be in the form of solid, semi-solid or liquid dosage forms, such as, for example, tablets, suppositories, pills, capsules, powders, liquids, suspensions, ointments or lotions, preferably in unit dosage form suitable for single administration of a precise dosage. The compositions can include an effective amount of the selected oligonucleotide-based compound in combination with a pharmaceutically acceptable carrier and, in addition, may include other pharmaceutical agents such as another therapeutic agent, adjuvants, diluents, buffers, and the like. The compounds may thus be administered in dosage formulations containing conventional non-toxic pharmaceutically acceptable carriers, adjuvants and vehicles. The amount of active compound administered will be dependent on the subject being treated, the subject's weight, the manner of administration and the judgment of the prescribing physician.

The present invention also provides a method of treating cancer, comprising administering to an individual a therapeutically effective amount of an oligonucleotide-based compound of the present invention, where the effector moiety comprises a molecule having anti-cancer activity and the regulating moiety inhibits or activates the anti-cancer activity of the effector moiety when the regulating and effector moieties interact. In preferred embodiments, the effector moiety comprises an enzyme and the regulating moiety comprises an inhibitor of the enzyme. In other embodiments, the effector moiety comprises a prodrug and the regulating moiety comprises an enzyme that converts the prodrug into a therapeutically active agent.

The present invention may be better understood by referring to the accompanying examples, which are intended for illustration purposes only and should not in any sense be construed as limiting the scope of the invention as defined in the claims appended hereto.

EXAMPLE 1

This example describes basic considerations for the design of the oligonucleotide-based compounds of the present invention, based on the embodiment shown in FIG. 1.

Since enzymes are responsible for supporting almost all of the chemical reactions involved in every life process, these proteins have become one of most important targets in drug discovery. There are many clinical drugs based on inhibiting the activity of enzymes. Well-known known examples of such drugs include methotrexate used in cancer chemotherapy to semi-selectively inhibit DNA synthesis of malignant cells, aspirin used to inhibit the synthesis of prostaglandins which are at least partly responsible for the aches and pains of arthritis, and sulfa drugs used to inhibit the folic acid synthesis that is essential for the metabolism and growth of disease-causing bacteria. Because inhibitors are such important potential drug candidates, many methods have been developed for their design. Among these methods, the structure-based methods are most successful (Anderson, A. C., The process of structure-based drug design. Chemistry & Biology, 2003. 10(9): p. 787-797; Klebe, G., Recent developments in structure-based drug design, Journal of Molecular Medicine-Jmm, 2000. 78(5): p. 269-281; both incorporated by reference herein). The structures used in the aid of inhibitor design include:

1. Transition state structure can be used as a guide to design new enzyme inhibitors. Based on transition-state theory suggested by Linus Pauling in 1940s, a transition-state intermediate exists between the substrates and products in an enzyme-catalyzed reaction. Typically, enzymes bind substrates and products with a dissociation constant between $10^{-3}$ to $10^{-6}$ M, while enzymes can bind the transition-state intermediate with a dissociation constant as low as $10^{-24}$ M. Therefore, if only a tiny fraction of that binding energy can be captured in a stable compound that mimics the transition-state intermediate, a potent inhibitor can be found.

2. Enzyme structure can be used to rationally design inhibitors. There are three primary methods for structure determination that are useful for inhibitor design: X-ray crystallography, NMR, and homology modeling. Structure-based design begins with the identification of a potential binding site on the enzyme. Ideally, the binding site is a pocket or protuberance with a variety of potential hydrogen bond donors and acceptors, hydrophobic characteristics, and sizes of molecular surfaces. Once the structure and target site are identified, either experimental or computational methods are used to design an inhibitor based on the structure of the enzyme. The high-throughput screening with combinatorial chemistry is a dominant experimental method for inhibitor discovery.

With the above methods, it is possible to design and identify inhibitors for the cytotoxic enzymes. Therefore, cytotoxic enzymes and their inhibitors can be good candidates for the effector and regulating moieties shown in FIG. 1. In order to improve specificity, the inhibitor is preferably noncompetitive, so the inhibition cannot be reversed by substrate.

EXAMPLE 2

This example describes basic considerations for the design of the oligonucleotide-based compounds of the present invention, based on the embodiment shown in FIG. 2.

Figure 6:
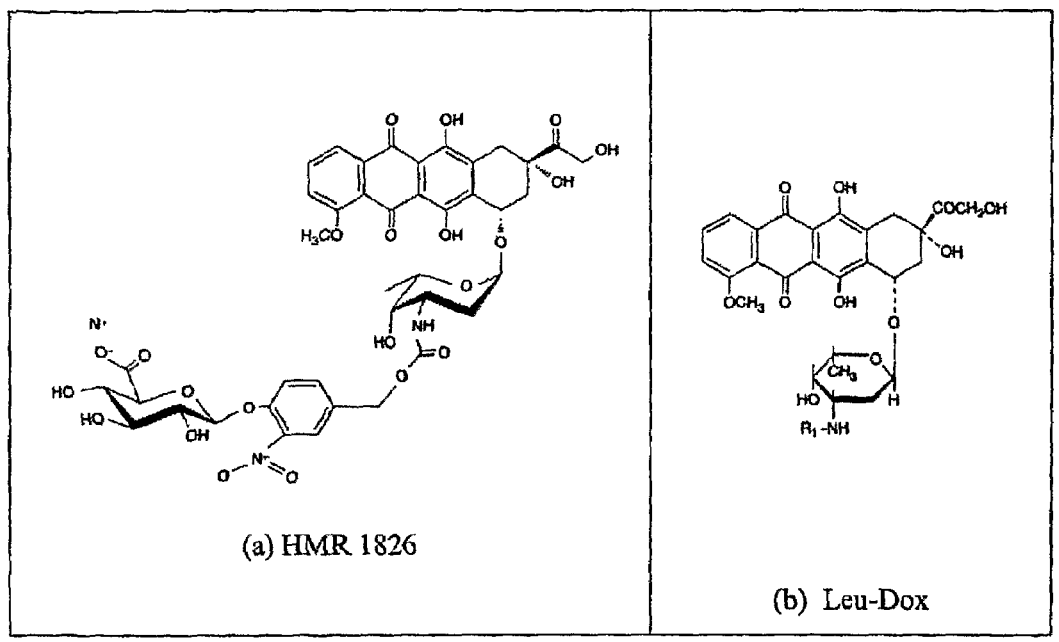
FIG. 6 provides the structures of two doxorubicin prodrugs.

Prodrugs are pharmacologically inert chemical derivatives that can be converted in vivo to the active drug molecules, enzymatically or nonenzymatically, to exert a therapeutic effect. In the last decade, numerous prodrugs that can be enzymatically activated into anti-cancer agents have been developed [Rooseboom, M., J. N. M. Commandeur, and N. P. E. Vermeulen, Enzyme-catalyzed activation of anticancer prodrugs, Pharmacological Reviews, 2004. 56(1): p. 53-102, incorporated by reference herein]. A prodrug is an inactive reversible chemical derivative of a drug and can be synthesized by covalently linking the drug with a chemical moiety. For example, doxorubicin is a DNA-damaging agent and can induce cell death through both p53-dependent and -independent pathways. Its commonly used therapeutic doses induce myelo-suppression and cumulative doses that exceed 550 mg/m$^2$ engender a substantial risk of cardiotoxicity. In order to reduce the toxicity of doxorubicin, several prodrugs have been developed. FIG. 6 shows two of such prodrugs. The one shown in FIG. 6(*a*), HMR 1826, contains glucuronic acid conjugated through a linker moiety to the aminoglycoside of doxorubicin. This prodrug can be converted to doxorubicin by β-glucuronidase, which is a lysosomal enzyme and is commonly found in the necrotic areas of tumors. The prodrug shown in FIG. 6(*b*), N-1-leucyl-doxorubucin (Leu-Dox), consists of a leucine amino acid conjugated to the primary amine of doxorubicin. The primary mechanism of prodrug activation at this site is lysis of the amino-peptidyl bond by intracellular lysosomal proteases, resulting in an intracellular conversion to free doxorubicin. Both of prodrugs have been shown to be more efficient anti-tumor agents than doxorubicin.

Each of these prodrugs can be attached to a hairpin-forming oligonucleotide as an effector moiety, while their respective converting enzymes, β-glucuronidase or lysosomal protease, can be attached as a regulating moiety. When a hairpin configuration is formed, the converting enzyme will can act on the prodrug, releasing the active agent doxorubicin.

EXAMPLE 3

This prospective example is based on the oligonucleotide-based compound shown in FIG. 1. The effector moiety can be a caspase protease (cystein aspartate-specific protease) listed in Table 1. Caspases can induce apoptosis in cancer cells. The regulatory moiety can be one of the caspase inhibitors listed in Table 1.

TABLE 1

| Caspases | Caspases Inhibitor (peptide sequence or name) |
|---|---|
| all caspases | Ac-Ala-Ala-Val-Ala-Leu-Leu-Pro-Ala-Val-Leu-Leu-Ala-Leu-Leu-Ala-Pro-Val-Ala-Asp-CHO (SEQ ID NO: 1) |
| Caspases-1 | Ac-Ala-Ala-Val-Ala-Leu-Leu-Pro-Ala-Val-Leu-Leu-Ala-Leu-Leu-Ala-Pro-Tyr-Val-Ala-Asp-CHO (SEQ ID NO: 2) |
| Caspases-2 | Ac-Leu-Asp-Glu-Ser-Asp-CHO (SEQ ID NO: 3) |
| Caspases-3 | Ac-Ala-Ala-Val-Ala-Leu-Leu-Pro-Ala-Val-Leu-Leu-Ala-Leu-Leu-Ala-Pro-Asp-Glu-Val-Asp-CHO (SEQ ID NO: 4) |

TABLE 1-continued

| Caspases | Caspases Inhibitor (peptide sequence or name) |
|---|---|
| Caspases-4 | Ac-Ala-Ala-Val-Ala-Leu-Leu-Pro-Ala-Val-Leu-Leu-Ala-Leu-Leu-Ala-Pro-Leu-Glu-Val-Asp-CHO (SEQ ID NO: 5) |
| Caspases-6 | Ac-Ala-Ala-Val-Ala-Leu-Leu-Pro-Ala-Val-Leu-Leu-Ala-Leu-Leu-Ala-Pro-Val-Glu-Ile-Asp-CHO (SEQ ID NO: 6) |
| Caspases-8 | Ac-Ala-Ala-Val-Ala-Leu-Leu-Pro-Ala-Val-Leu-Leu-Ala-Leu-Leu-Ala-Pro-Ile-Glu-Thr-Asp-CHO (SEQ ID NO: 7) |
| Caspases-9 | Ac-Ala-Ala-Val-Ala-Leu-Leu-Pro-Ala-Val-Leu-Leu-Ala-Leu-Leu-Ala-Pro-Leu-Glu-His-Asp-CHO (SEQ ID NO: 8) |
| Caspases-13 | Ac-Leu-Glu-Glu-Asp-CHO (SEQ ID NO: 9) |
| Caspases-3, Caspases-7 | 5-[(S)-(+)-2-(Methoxymethyl)pyrrolidino]sulfonylisatin |

The biomarker can be a cancer cell biomarker. When the biomarker is absent, the oligonucleotide-based compound can be in the hairpin configuration, and the caspase can be inhibited. When the biomarker is present, the open configuration is assumed, and the caspase can be active. Active caspase can induce apoptosis, which can kill the cancer cell.

EXAMPLE 4

This prospective example is based on the oligonucleotide-based compound shown in FIG. 2. The effector moiety can be a prodrug listed in Table 2. The regulatory moiety can be one of the activation enzymes listed in Table 2, which is derived from Rooseboom, M., J. N. M. Commandeur, and N. P. E. Vermeulen, Enzyme-catalyzed activation of anticancer prodrugs, Pharmacological Reviews, 2004. 56(1): p. 53-102.

TABLE 2

| Activation enzyme | Prodrug | Drug |
|---|---|---|
| Nitroreductase | CB 1954 | 5-(Aziridin-1-yl)-4-hydroxyl-amino-2-nitro-benzamide |
| Cytochrome P450 | 4-Ipomeanol | Unidentified (furan epoxide is speculated) |
| Cytochrome P450 | Ifosfamide | Isophosphoramide mustard |
| Cytochrome P450 | Cyclophosphamide | Phosphoramide mustard |
| Purine-nucleoside phosphorylase | Fludarabine | 2-Fluoroadenine |
| Purine-nucleoside phosphorylase | MeP-dR | MeP |
| Thymidine kinase | Ganciclovir | Ganciclovir-triphosphate nucleotide |
| Alkaline phosphatase | Etoposide phosphate | Etoposide |
| Alkaline phosphatase | Mitomycin C phosphate | Mitomycin C |
| Alkaline phosphatase | POMP | POM |
| Alkaline phosphatase | N-(4-phosphonooxy)-phenylacetyl)doxorubicin | Doxorubicin |
| β-Glucuronidase | Glucuronidated Nornitrogen mustard | Oxazolidinone |
| β-Glucuronidase | Glucuronidated 9-amino-camptothecin | 9-Aminocamptothecin |
| β-Glucuronidase | Glucuronide mustard | Mustard |
| Carboxypeptidase | Methotrexate-amino acids | Methotrexate |
| Carboxypeptidase | CMDA | Benzoic acid mustard |
| Penicillin amidase | DPO | Doxorubicin |
| Penicillin amidase | MelPO | Melphalan |
| Penicillin amidase | NHPAP | Palytoxin |
| Penicillin amidase | N-(phenylacetyl) doxorubicin | Doxorubicin |
| Penicillin amidase | N-(phenylacetyl) melphalan | Melphalan |

TABLE 2-continued

| Activation enzyme | Prodrug | Drug |
|---|---|---|
| β-Lactamase | C-DOX | Doxorubicin |
| β-Lactamase | PRODOX | Doxorubicin |
| β-Lactamase | CM | Phenylenediamine mustard |
| β-Lactamase | CCM | Phenylenediamine mustard |
| β-Lactamase | Cephalosporin-DACCP | DACCP |
| β-Lactamase | PROTAX | Taxol |
| β-Lactamase | Cephalosporin mitomycin C | Mitomycin C |
| β-Lactamase | C-Mel | Melphalan |
| Cytosine deaminase | 5-Fluorocytosine | 5-Fluorouracil |
| Methionine γ-lyase | Selenomethionine | Methylselenol |
| Methionine γ-lyase | Trifluoromethionine | CSF2 |

In Table 2, MeP is 6-methylpurine; POMP is p-N,N-bis(2-chloroethyl)aminophenyl phosphate; POM is p-N,N-bis(2-chloroethyl)aminophenol; DAVLBHYD is 4-desacetylvinblastine-3-carboxylic acid hydrazide; DACCP is 4-carboxyphthalato(1,2-cyclohexanediamine) platinum; and CSF2 is carbonothionic difluoride.

The biomarker can be a cancer cell biomarker. When the biomarker is absent, the oligonucleotide-based compound can be bound to its binding partner, and can be in the open configuration. When the biomarker is present, the hairpin configuration can be assumed, and the activating enzyme can act on the prodrug, releasing active drug.

EXAMPLE 5

This prospective example shows various biomarker and loop sequences for the an oligonucleotide-based compound shown in FIG. 1. The biomarker is based on the ras gene, which is the most frequently mutated oncogenes in human cancers. In inducible K-ras4bG$^{G12D}$ transgenic mice, it has been shown that induction of K-ras4b$^{G12D}$ oncogene in the basal layer of the epidermis cause formation of malignant SCC in the skin and other squamous epithelia. The mRNA of K-ras4b$^{G12D}$ can be used as biomarker.

Table 3 lists the cDNA sequence of K-ras and the G12D mutant of K-ras. All nucleotide sequences in this and the following tables are listed conventionally in the 5'-3' direction.

TABLE 3

```
Wild:                                    (SEQ ID NO: 10)
ATGACTGAGT ATAAACTTGT GGTGGTTGGA GCTGGTGGCG

TAGGCAAGAG CGCCTTGACG ATACAGCTAA TTCAGAATCA

CTTTGTGGAT GAGTACGACC CTACGATAGA GGACTGCTAC

AGGAAACAAG TAGTAATTGA TGGAGAAACC TGTCTCTTGG

ATATTCTCGA CACAGCAGGT CAAGAGGAGT ACAGTGCAAT

GAGGGACCAG TACATGAGAA CTGGGGAGGG CTTTCTTTGT

GTATTTGCCA TAAATAATAC TAAATCATTT GAAGATATTC

ACCATTATAG AGAACAAATT AAAAGAGTAA AGGACTCTGA

AGATGTGCCT ATGGTCCTGG TAGGGAATAA GTGTGATTTG

CCTTCTAGAA CAGTAGACAC GAAACAGGCT CAGGAGTTAG

CAAGGAGTTA CGGGATTCCG TTCATTGAGA CCTCAGCAAA
```

TABLE 3-continued

```
GACAAGACAG GGTGTTGACG ATGCCTTCTA TACATTAGTC

CGAGAAATTC GAAAACATAA AGAAAAGATG AGCAAAGATG

GGAAGAAGAA GAAGAAGAAG TCAAGGACAA GGTGTACAGT

TATGTGA

G12D Mutant:                             (SEQ ID NO: 11)
ATGACTGAGT ATAAACTTGT GGTGGTTGGA GCTGATGGCG

TAGGCAAGAG CGCCTTGACG ATACAGCTAA TTCAGAATCA

CTTTGTGGAT GAGTACGACC CTACGATAGA GGACTCCTAC

AGGAAACAAG TAGTAATTGA TGGAGAAACC TGTCTCTTGG

ATATTCTCGA CACAGCAGGT CAAGAGGAGT ACAGTGCAAT

GAGGGACCAG TACATGAGAA CTGGGGAGGG CTTTCTTTGT

GTATTTGCCA TAAATAATAC TAAATCATTT GAAGATATTC

ACCATTATAG AGAACAAATT AAAAGAGTAA AGGACTCTGA

AGATGTGCCT ATGGTCCTGG TAGGGAATAA GTGTGATTTG

CCTTCTAGAA CAGTAGACAC GAAACAGGCT CAGGAGTTAG

CAAGGAGTTA CGGGATTCCG TTCATTGAGA CCTCAGCAAA

GACAAGACAG GGTGTTGACG ATGCCTTCTA TACATTAGTC

CGAGAAATTC GAAAACATAA AGAAAAGATG AGCAAAGATG

GGAAGAAGAA GAAGAAGAAG TCAAGGACAA GGTGTACAGT

TATGTGA
```

The possible sequences for the loop are shown in Table 4.

TABLE 4

| No. | Loop | |
|---|---|---|
| #1 | CGCCAUCAGCUCCAACCACC | (SEQ ID NO: 12) |
| #2 | GCCAUCAGCUCCAACCACCA | (SEQ ID NO: 13) |
| #3 | UGCCUACGCCAUCAGCUCCA | (SEQ ID NO: 14) |
| #4 | UUGCCUACGCCAUCAGCUCC | (SEQ ID NO: 15) |
| #5 | ACGCCAUCAGCUCCAACCAC | (SEQ ID NO: 16) |
| #6 | CCAUCAGCUCCAACCACCAC | (SEQ ID NO: 17) |
| #7 | UACGCCAUCAGCUCCAACCA | (SEQ ID NO: 18) |
| #8 | CUACGCCAUCAGCUCCAACC | (SEQ ID NO: 19) |
| #9 | GCCUACGCCAUCAGCUCCAA | (SEQ ID NO: 20) |
| #10 | CUUGCCUACGCCAUCAGCUC | (SEQ ID NO: 21) |
| #11 | UCUUGCCUACGCCAUCAGCU | (SEQ ID NO: 22) |
| #12 | CUCUUGCCUACGCCAUCAGC | (SEQ ID NO: 23) |
| #13 | CCUACGCCAUCAGCUCCAAC | (SEQ ID NO: 24) |

Stems can be designed for each loop. For example, stems (underlined) and possible loop sequences, based on Loop #9, are shown in Table 5.

TABLE 5

UCCGCGCCUACGCCAUCAGCUCCAAGCGGA (SEQ ID NO: 25)

ACCGCGCCUACGCCAUCAGCUCCAAGCGGU (SEQ ID NO: 26)

CACCCGCCUACGCCAUCAGCUCCAAGGGUG (SEQ ID NO: 27)

CACCGGCCUACGCCAUCAGCUCCAACGGUG (SEQ ID NO: 28)

CCCGAGCCUACGCCAUCAGCUCCAAUCGGG (SEQ ID NO: 29)

CCCGUGCCUACGCCAUCAGCUCCAAACGGG (SEQ ID NO: 30)

CCGACGCCUACGCCAUCAGCUCCAAGUCGG (SEQ ID NO: 31)

CCUGCGCCUACGCCAUCAGCUCCAAGCAGG (SEQ ID NO: 32)

EXAMPLE 6

This prospective example shows various loop and binding partner sequences for an oligonucleotide-based compound shown in FIG. 2. As in Example 5, the biomarker is based on the ras gene.

Table 6 shows possible sequences for the binding partner sequences and the corresponding loop sequences.

TABLE 6

| | Binding Partner Oligo | Loop sequence |
|---|---|---|
| #1 | CGCCAUCAGCUCCAACCACC (SEQ ID NO: 33) | GUGGUUGGAGCUGAUGGC (SEQ ID NO: 46) |
| #2 | GCCAUCAGCUCCAACCACCA (SEQ ID NO: 34) | GGUGGUUGGAGCUGAUGG (SEQ ID NO: 47) |
| #3 | UGCCUACGCCAUCAGCUCCA (SEQ ID NO: 35) | GGAGCUGAUGGCGUAGGC (SEQ ID NO: 48) |
| #4 | UUGCCUACGCCAUCAGCUCC (SEQ ID NO: 36) | GAGCUGAUGGCGUAGGCA (SEQ ID NO: 49) |
| #5 | ACGCCAUCAGCUCCAACCAC (SEQ ID NO: 37) | UGGUUGGAGCUGAUGGCG (SEQ ID NO: 50) |
| #6 | CCAUCAGCUCCAACCACCAC (SEQ ID NO: 38) | UGGUGGUUGGAGCUGAUG (SEQ ID NO: 51) |
| #7 | UACGCCAUCAGCUCCAACCA (SEQ ID NO: 39) | GGUUGGAGCUGAUGGCGU (SEQ ID NO: 52) |
| #8 | CUACGCCAUCAGCUCCAACC (SEQ ID NO: 40) | GUUGGAGCUGAUGGCGUA (SEQ ID NO: 53) |

TABLE 6-continued

| | Binding Partner Oligo | Loop sequence |
|---|---|---|
| #9 | GCCUACGCCAUCAGCUCCAA (SEQ ID NO: 41) | UGGAGCUGAUGGCGUAGG (SEQ ID NO: 54) |
| #10 | CUUGCCUACGCCAUCAGCUC (SEQ ID NO: 42) | AGCUGAUGGCGUAGGCAA (SEQ ID NO: 55) |
| #11 | UCUUGCCUACGCCAUCAGCU (SEQ ID NO: 43) | GCUGAUGGCGUAGGCAAG (SEQ ID NO: 56) |
| #12 | CUCUUGCCUACGCCAUCAGC (SEQ ID NO: 44) | CUGAUGGCGUAGGCAAGA (SEQ ID NO: 57) |
| #13 | CCUACGCCAUCAGCUCCAAC (SEQ ID NO: 45) | UUGGAGCUGAUGGCGUAG. (SEQ ID NO: 58) |

Table 7 shows possible loop and stem (underlined) sequences for oligonucleotide-based compounds, based on Table 6.

TABLE 7

UCCGCUGGAGCUGAUGGCGUAGGGCGGA (SEQ ID NO: 59)

ACCGCUGGAGCUGAUGGCGUAGGGCGGU (SEQ ID NO: 60)

CACCCUGGAGCUGAUGGCGUAGGGGGUG (SEQ ID NO: 61)

CACCGUGGAGCUGAUGGCGUAGGCGGUG (SEQ ID NO: 62)

CCCGAUGGAGCUGAUGGCGUAGGUCGGG (SEQ ID NO: 63)

CCCGUUGGAGCUGAUGGCGUAGGACGGG (SEQ ID NO: 64)

CCGACUGGAGCUGAUGGCGUAGGGUCGG (SEQ ID NO: 65)

CCUGCUGGAGCUGAUGGCGUAGGGCAGG. (SEQ ID NO: 66)

EXAMPLE 7

The following contributions to free energy change can be considered in the design of oligonucleotide-based compounds shown in FIG. 1: drug and inhibitor complex breakage, loop self-structure breakage, biomarker self-structure breakage, and loop and biomarker complex formation.

The following contributions to free energy change can be considered in the design of oligonucleotide-based compounds shown in FIG. 2: loop and binding partner complex breakage, diagnosis loop self-structure formation, drug and activator complex formation, biomarker self-structure breakage, and binding partner and biomarker complex formation.

---

What is claimed is:

1. A method of controlling the activity of a biologically active compound, comprising:
   a) providing a hairpin-forming oligonucleotide capable of existing in either a hairpin configuration having a single-stranded loop and a double-stranded stem, or an open configuration lacking the double-stranded stem;
   b) physically associating an effector moiety with the oligonucleotide, said effector moiety having a biological activity;
   c) physically associating a regulating moiety with the oligonucleotide, said regulating moiety controlling the biological activity of the effector moiety when the regulating and effector moieties interact; and
   d) changing from one configuration to the other;
   wherein the regulating moiety interacts with the effector moiety when the oligonucleotide is in the hairpin configuration, and the regulating and effector moieties fail to interact when the oligonucleotide is in the open configuration, and
   wherein the biological activity comprises sterically blocking a target molecule.

2. The method of claim 1, wherein the biological activity is a therapeutic activity.

3. The method of claim 1, wherein the regulating moiety activates the biological activity of the effector moiety.

4. The method of claim 1, wherein the regulating moiety inhibits the biological activity of the effector moiety.

5. The method of claim 1, wherein binding of the loop to a biomarker causes the oligonucleotide to assume its open configuration, whereby the biological activity of the effector moiety is expressed.

6. The method of claim 5, wherein the biomarker is a protein or a nucleic acid.

7. The method of claim 1, further comprising providing a binding partner that binds to the loop, thereby causing the oligonucleotide to assume its open configuration.

8. The method of claim 7, wherein the binding partner is a protein or a nucleic acid.

9. The method of claim 7, wherein binding of a biomarker to the binding partner causes the oligonucleotide to assume its hairpin configuration, whereby the biological activity of the effector moiety is expressed.

10. The method of claim 1, wherein the effector moiety comprises an enzyme and the regulating moiety inhibits the enzyme when the oligonucleotide is in the hairpin configuration.

11. The method of claim 1, wherein the effector moiety comprises a prodrug and the regulating moiety converts the prodrug into a therapeutically active agent when the oligonucleotide is in the hairpin configuration.

12. The method of claim 1, wherein the effector moiety comprises an antisense molecule making up at least a portion of one strand of the duplex stem, and the regulating moiety comprises at least a portion of the other strand of the duplex stem and is complementary to the antisense molecule.

13. The method of claim 1, wherein the effector moiety comprises a nanofabricated container enclosing molecules having at least one biological activity, and the regulating moiety prevents the release of the molecules from the container when the oligonucleotide is in the hairpin configuration.

14. A method of controlling the activity of a biologically active compound, comprising:
   a) providing a hairpin-forming oligonucleotide capable of existing in either a hairpin configuration having a single-stranded loop and a double-stranded stem, or an open configuration lacking the double-stranded stem;
   b) attaching an effector moiety to the oligonucleotide, said effector moiety having a therapeutic activity;
   c) attaching a regulating moiety to the oligonucleotide, said regulating moiety inhibiting or activating the therapeutic activity of the effector moiety when the regulating and effector moieties interact; and
   d) changing from one configuration to the other;
   wherein the regulating moiety interacts with the effector moiety when the oligonucleotide is in the hairpin configuration, and the regulating and effector moieties fail to interact when the oligonucleotide is in the open configuration, and
   wherein the therapeutic activity comprises sterically blocking a target molecule.

15. The method of claim 14, wherein binding of the loop to a biomarker causes the oligonucleotide to assume its open configuration, whereby the therapeutic activity of the effector moiety is expressed.

16. The method of claim 15, wherein the effector moiety is an enzyme and the regulating moiety inhibits the enzyme when the oligonucleotide is in the hairpin configuration.

17. The method of claim 14, further comprising providing a binding partner that binds to the loop, thereby causing the oligonucleotide to assume its open configuration.

18. The method of claim 17, wherein binding of a biomarker to the binding partner causes the oligonucleotide to assume its hairpin configuration, whereby the therapeutic activity of the effector moiety is expressed.

19. The method of claim 18, wherein the effector moiety comprises a prodrug and the regulating moiety converts the prodrug into a therapeutically active agent when the oligonucleotide is in the hairpin configuration.

* * * * *

SEQUENCE LISTING

<160> NUMBER OF SEQ ID NOS: 66

<210> SEQ ID NO 1
<211> LENGTH: 19
<212> TYPE: PRT
<213> ORGANISM: Artificial Sequence
<220> FEATURE:

<223> OTHER INFORMATION: Caspases inhibitor

<400> SEQUENCE: 1

Ala Ala Val Ala Leu Leu Pro Ala Val Leu Leu Ala Leu Leu Ala Pro
1               5                   10                  15

Val Ala Asp

<210> SEQ ID NO 2
<211> LENGTH: 20
<212> TYPE: PRT
<213> ORGANISM: Artificial Sequence
<220> FEATURE:
<223> OTHER INFORMATION: Caspases inhibitor

<400> SEQUENCE: 2

Ala Ala Val Ala Leu Leu Pro Ala Val Leu Leu Ala Leu Leu Ala Pro
1               5                   10                  15

Tyr Val Ala Asp
            20

<210> SEQ ID NO 3
<211> LENGTH: 5
<212> TYPE: PRT
<213> ORGANISM: Artificial Sequence
<220> FEATURE:
<223> OTHER INFORMATION: Caspases inhibitor

<400> SEQUENCE: 3

Leu Asp Glu Ser Asp
1               5

<210> SEQ ID NO 4
<211> LENGTH: 20
<212> TYPE: PRT
<213> ORGANISM: Artificial Sequence
<220> FEATURE:
<223> OTHER INFORMATION: Caspases inhibitor

<400> SEQUENCE: 4

Ala Ala Val Ala Leu Leu Pro Ala Val Leu Leu Ala Leu Leu Ala Pro
1               5                   10                  15

Asp Glu Val Asp
            20

<210> SEQ ID NO 5
<211> LENGTH: 20
<212> TYPE: PRT
<213> ORGANISM: Artificial Sequence
<220> FEATURE:
<223> OTHER INFORMATION: Caspases inhibitor

<400> SEQUENCE: 5

Ala Ala Val Ala Leu Leu Pro Ala Val Leu Leu Ala Leu Leu Ala Pro
1               5                   10                  15

Leu Glu Val Asp
            20

<210> SEQ ID NO 6
<211> LENGTH: 20
<212> TYPE: PRT
<213> ORGANISM: Artificial Sequence
<220> FEATURE:
<223> OTHER INFORMATION: Caspases inhibitor

<400> SEQUENCE: 6

```
Ala Ala Val Ala Leu Leu Pro Ala Val Leu Leu Ala Leu Leu Ala Pro
1               5                   10                  15

Val Glu Ile Asp
            20

<210> SEQ ID NO 7
<211> LENGTH: 20
<212> TYPE: PRT
<213> ORGANISM: Artificial Sequence
<220> FEATURE:
<223> OTHER INFORMATION: Caspases inhibitor

<400> SEQUENCE: 7

Ala Ala Val Ala Leu Leu Pro Ala Val Leu Leu Ala Leu Leu Ala Pro
1               5                   10                  15

Ile Glu Thr Asp
            20

<210> SEQ ID NO 8
<211> LENGTH: 20
<212> TYPE: PRT
<213> ORGANISM: Artificial Sequence
<220> FEATURE:
<223> OTHER INFORMATION: Caspases inhibitor

<400> SEQUENCE: 8

Ala Ala Val Ala Leu Leu Pro Ala Val Leu Leu Ala Leu Leu Ala Pro
1               5                   10                  15

Leu Glu His Asp
            20

<210> SEQ ID NO 9
<211> LENGTH: 4
<212> TYPE: PRT
<213> ORGANISM: Artificial Sequence
<220> FEATURE:
<223> OTHER INFORMATION: Caspases inhibitor

<400> SEQUENCE: 9

Leu Glu Glu Asp
1

<210> SEQ ID NO 10
<211> LENGTH: 567
<212> TYPE: DNA
<213> ORGANISM: Artificial Sequence
<220> FEATURE:
<223> OTHER INFORMATION: Transgenic mouse expressing K-ras4bG12D

<400> SEQUENCE: 10
atgactgagt ataaacttgt ggtggttgga gctggtggcg taggcaagag cgccttgacg      60
atacagctaa ttcagaatca ctttgtggat gagtacgacc ctacgataga ggactcctac     120
aggaaacaag tagtaattga tggagaaacc tgtctcttgg atattctcga cacagcaggt     180
caagaggagt acagtgcaat gagggaccag tacatgagaa ctggggaggg ctttctttgt     240
gtatttgcca taataatac taaatcattt gaagatattc accattatag agaacaaatt     300
aaaagagtaa aggactctga agatgtgcct atggtcctgg tagggaataa gtgtgatttg     360
ccttctagaa cagtagacac gaaacaggct caggagttag caaggagtta cgggattccg     420
ttcattgaga cctcagcaaa gacaagacag ggtgttgacg atgccttcta tacattagtc     480
cgagaaattc gaaacataa agaaagatg agcaaagatg gaagaagaa gaagaagaag     540 tcaaggacaa ggtgtacagt tatgtga                                         567
```

```
<210> SEQ ID NO 11
<211> LENGTH: 567
<212> TYPE: DNA
<213> ORGANISM: Artificial Sequence
<220> FEATURE:
<223> OTHER INFORMATION: Transgenic mouse expressing K-ras4bG12D

<400> SEQUENCE: 11
atgactgagt ataaacttgt ggtggttgga gctgatggcg taggcaagag cgccttgacg      60
atacagctaa ttcagaatca ctttgtggat gagtacgacc ctacgataga ggactcctac     120
aggaaacaag tagtaattga tggagaaacc tgtctcttgg atattctcga cacagcaggt     180
caagaggagt acagtgcaat gagggaccag tacatgagaa ctggggaggg ctttctttgt     240
gtatttgcca taataatac taaatcattt gaagatattc accattatag agaacaaatt      300
aaaagagtaa aggactctga agatgtgcct atggtcctgg tagggaataa gtgtgatttg     360
ccttctagaa cagtagacac gaaacaggct caggagttag caaggagtta cgggattccg     420
ttcattgaga cctcagcaaa gacaagacag ggtgttgacg atgccttcta tacattagtc     480
cgagaaattc gaaaacataa agaaaagatg agcaaagatg ggaagaagaa gaagaagaag     540
tcaaggacaa ggtgtacagt tatgtga                                         567

<210> SEQ ID NO 12
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 12
cgccaucagc uccaaccacc                                                  20

<210> SEQ ID NO 13
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 13
gccaucagcu ccaaccacca                                                  20

<210> SEQ ID NO 14
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 14
ugccuacgcc aucagcucca                                                  20

<210> SEQ ID NO 15
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 15
uugccuacgc caucagcucc                                                  20
```

```
<210> SEQ ID NO 16
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 16
acgccaucag cuccaaccac                                                   20

<210> SEQ ID NO 17
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 17
ccaucagcuc caaccaccac                                                   20

<210> SEQ ID NO 18
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 18
uacgccauca gcuccaacca                                                   20

<210> SEQ ID NO 19
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 19
cuacgccauc agcuccaacc                                                   20

<210> SEQ ID NO 20
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 20
gccuacgcca ucagcuccaa                                                   20

<210> SEQ ID NO 21
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 21
cuugccuacg ccaucagcuc                                                   20

<210> SEQ ID NO 22
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 22
```

```
ucuugccuac gccaucagcu                                              20

<210> SEQ ID NO 23
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 23
cucuugccua cgccaucagc                                              20

<210> SEQ ID NO 24
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 24
ccuacgccau cagcuccaac                                              20

<210> SEQ ID NO 25
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 25
uccgcgccua cgccaucagc uccaagcgga                                   30

<210> SEQ ID NO 26
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 26
accgcgccua cgccaucagc uccaagcggu                                   30

<210> SEQ ID NO 27
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 27
cacccgccua cgccaucagc uccaagggug                                   30

<210> SEQ ID NO 28
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 28
caccggccua cgccaucagc uccaacggug                                   30
```

```
<210> SEQ ID NO 29
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 29
cccgagccua cgccaucagc uccaaucggg                                      30

<210> SEQ ID NO 30
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 30
cccgugccua cgccaucagc uccaaacggg                                      30

<210> SEQ ID NO 31
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 31
ccgacgccua cgccaucagc uccaagucgg                                      30

<210> SEQ ID NO 32
<211> LENGTH: 30
<212> TYPE: RNA
<213> ORGANISM: Artificial Sequence
<220> FEATURE:
<223> OTHER INFORMATION: Sequence of loop SEQ ID NO.: 9 caspeses
      inhibitor plus stems on opposite sides thereof

<400> SEQUENCE: 32
ccugcgccua cgccaucagc uccaagcagg                                      30

<210> SEQ ID NO 33
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 33
cgccaucagc uccaaccacc                                                 20

<210> SEQ ID NO 34
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 34
gccaucagcu ccaaccacca                                                 20

<210> SEQ ID NO 35
<211> LENGTH: 20
<212> TYPE: RNA
<213> ORGANISM: Artificial Sequence
```

```
<220> FEATURE:
<223> OTHER INFORMATION: Transgenic mouse expressing K-ras4bG12D

<400> SEQUENCE: 35
ugccuacgcc aucagcucca                                               20

<210> SEQ ID NO 36
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 36
uugccuacgc caucagcucc                                               20

<210> SEQ ID NO 37
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 37
acgccaucag cuccaaccac                                               20

<210> SEQ ID NO 38
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 38
ccaucagcuc caaccaccac                                               20

<210> SEQ ID NO 39
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 39
uacgccauca gcuccaacca                                               20

<210> SEQ ID NO 40
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 40
cuacgccauc agcuccaacc                                               20

<210> SEQ ID NO 41
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 41
gccuacgcca ucagcuccaa                                               20
```

```
<210> SEQ ID NO 42
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 42
cuugccuacg ccaucagcuc                                            20

<210> SEQ ID NO 43
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 43
ucuugccuac gccaucagcu                                            20

<210> SEQ ID NO 44
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 44
cucuugccua cgccaucagc                                            20

<210> SEQ ID NO 45
<211> LENGTH: 20
<212> TYPE: RNA
<213> ORGANISM: Artificial Sequence
<220> FEATURE:
<223> OTHER INFORMATION: Transgenic mouse expressing K-ras4bG12D

<400> SEQUENCE: 45
ccuacgccau cagcuccaac                                            20

<210> SEQ ID NO 46
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 46
gugguuggag cugauggc                                              18

<210> SEQ ID NO 47
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 47
ggugguugga gcugaugg                                              18

<210> SEQ ID NO 48
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 48
```

```
ggagcugaug gcguaggc                                                    18

<210> SEQ ID NO 49
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 49
gagcugaugg cguaggca                                                    18

<210> SEQ ID NO 50
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 50
ugguuggagc ugauggcg                                                    18

<210> SEQ ID NO 51
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 51
uggugguugg agcugaug                                                    18

<210> SEQ ID NO 52
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 52
gguuggagcu gauggcgu                                                    18

<210> SEQ ID NO 53
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 53
guuggagcug auggcgua                                                    18

<210> SEQ ID NO 54
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 54
uggagcugau ggcguagg                                                    18

<210> SEQ ID NO 55
<211> LENGTH: 18
<212> TYPE: RNA
<213> ORGANISM: Artificial Sequence
```

```
<220> FEATURE:
<223> OTHER INFORMATION: Transgenic mouse expressing K-ras4bG12D

<400> SEQUENCE: 55
agcugauggc guaggcaa                                                  18

<210> SEQ ID NO 56
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 56
gcugauggcg uaggcaag                                                  18

<210> SEQ ID NO 57
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 57
cugauggcgu aggcaaga                                                  18

<210> SEQ ID NO 58
<211> LENGTH: 18
<212> TYPE: RNA
<213> ORGANISM: Artificial Sequence
<220> FEATURE:
<223> OTHER INFORMATION: Transgenic mouse expressing K-ras4bG12D

<400> SEQUENCE: 58
uuggagcuga uggcguag                                                  18

<210> SEQ ID NO 59
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 59
uccgcuggag cugauggcgu agggcgga                                       28

<210> SEQ ID NO 60
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 60
accgcuggag cugauggcgu agggcggu                                       28

<210> SEQ ID NO 61
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof
```

```
<400> SEQUENCE: 61
cacccuggag cugauggcgu agggggug                                    28

<210> SEQ ID NO 62
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 62
caccguggag cugauggcgu aggcggug                                    28

<210> SEQ ID NO 63
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 63
cccgauggag cugauggcgu aggucggg                                    28

<210> SEQ ID NO 64
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 64
cccguuggag cugauggcgu aggacggg                                    28

<210> SEQ ID NO 65
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 65
ccgacuggag cugauggcgu agggucgg                                    28

<210> SEQ ID NO 66
<211> LENGTH: 28
<212> TYPE: RNA
<213> ORGANISM: Artificial Sequence
<220> FEATURE:
<223> OTHER INFORMATION: Sequence of loop SEQ ID NO.: 58 transgenic
      mouse, eliminating u at the 5' end, plus stems on opposite sides
      thereof

<400> SEQUENCE: 66
ccugcuggag cugauggcgu agggcagg                                    28
```